United States Patent [19]
Sakai et al.

[11] Patent Number: 6,117,853
[45] Date of Patent: Sep. 12, 2000

[54] CEREBRATION IMPROVER

[75] Inventors: Masashi Sakai; Hideyuki Yamatoya; Naomi Mizusawa; Satoshi Kudo, all of Tokyo, Japan

[73] Assignee: Kabushiki Kaisha Yakult Honsha, Tokyo, Japan

[21] Appl. No.: 09/228,938

[22] Filed: Jan. 12, 1999

Related U.S. Application Data

[62] Division of application No. 08/556,862, Nov. 2, 1995, Pat. No. 5,900,409.

[30]    Foreign Application Priority Data

Nov. 8, 1994    [JP]    Japan    .................................    6-297998

[51] Int. Cl.$^7$ .......................... A61K 31/685; A61K 31/20
[52] U.S. Cl. ............................ 514/78; 514/558; 514/560
[58] Field of Search ............................... 514/78, 558, 560

[56]    References Cited

U.S. PATENT DOCUMENTS

| | | |
|---|---|---|
| 4,385,053 | 5/1983 | Reisberg et al. . |
| 5,001,117 | 3/1991 | Hirsch . |

FOREIGN PATENT DOCUMENTS

| | | |
|---|---|---|
| 0 396 080 | 11/1990 | European Pat. Off. . |
| 41 17 629 | 12/1992 | Germany . |
| 4117629 | 12/1992 | Germany . |
| 63-245685 | 10/1988 | Japan . |
| 1-135720 | 5/1989 | Japan . |
| 2-306982 | 12/1990 | Japan . |
| 6-256179 | 9/1994 | Japan . |
| 6-279311 | 10/1994 | Japan . |
| 7-35389 | 4/1995 | Japan . |
| 9405319 | 3/1994 | WIPO . |

OTHER PUBLICATIONS

A. Zanotti et al., "Chronic phosphatidylserine treatment improves spatial memory and passive avoidance in aged rats", *Psychopharmacology*, (1989) 99:316–321.

P.J. Delwaide et al., "Double–blind randomized controlled study of phosphatidylserine in senile demented patients", *Acta Neurol. Scand.*, vol. 73, 1986, pp. 136–140.

Rolf R. Engel, Double–blind cross–over study of phosphatidylserine vs. placebo in patients with early dementia of the Alzeheimer type, *European Neuropsychopharmacology*, 2 (1992), pp. 149–155.

T. Cenacchi et al., "Cognitive decline in the elderly: A double–blind, placebo–controlled multicenter study on efficacy of phosphatidylserine administration", *Aging Clin. Exp. Res.*, 5, 1993, pp. 123–133.

Hyeun Wook Chang et al., "Stereoselective effects of lysophosphatidylserine in rodents", *Br. J. Pharmacol.*, (1988), 93, pp. 647–653.

A. Bruni et al., "Pharmacological effects of phosphatidylserine liposomes", *Nature*, vol. 260, 1976, pp. 331–333.

Database WPI, Section Ch, Week 8927, Derwent Publications Ltd., London, GB; Class B05, AN 89–197154, XP002015464 of JP–A–01 135 720 (EISAI KK), May 29, 1989.

Database WPI, Section Ch, Week 9444, Derwent Publications Ltd., London, GB; Class B05, AN 94–354659, XP002015465 of JP–A–06 279 311 (NIPPON SHOJI KK), Oct. 4, 1994.

Yumiko Tamori–Natori et al, "Metabolism of Lysophosphatidylserine, a Potentiator of Histamine Release in Rat Mast Cells", *J. Biochem.*, vol. 100, No. 3, 1986, pp. 581–590.

E. Bigon et al, "Pharmacological Effects of Phosphatidylserine Liposomes: The Role of Lysophosphatidylserine", *BR. J. Pharmacol.*, vol. 67, 1979, pp. 611–616.

Hyeun Wook Chang et al, "Stereoselective Effects of Lysophosphatidylserine in Rodents", *BR. J. Pharmacol.*, vol. 93, No. 3, 1988, pp. 647–653.

Satoshi Shuto et al, "A Facile One–Step Synthesis of Phosphatidylhomoserines by Phospholipase D–Catalyzed Transphosphatidylation", *Chem. Pharm. Bull.*, vol. 35, No. 1, 1987, pp. 447–449.

Dr. Herbert P. Fiedler, "Lexikon der Hilfsstoffe für Pharmazie, Kosmetik und angrenzende Gebiete", 1989, EDITIO CANTOR AULENDORF, pp. 731–732, p. 1059, p. 1119.

*Primary Examiner*—Kevin E. Weddington
*Attorney, Agent, or Firm*—Frishauf, Holtz, Goodman, Langer & Chick, P.C.

[57]    ABSTRACT

A cerebration improver having a prominent action for increasing brain glucose level has an effect of improving the cerebration of a subject administered with the improver. The cerebration improver contains as the effective ingredient phosphatidyl-L-serine, or lysophosphatidyl-L-serine produced by eliminating the fatty acid chain at the position α or β of phosphatidyl-L-serine, or the salts thereof. The phosphatidyl-L-serine has a structural fatty acid chain derived from at least one raw material lecithin selected from the group consisting of soy bean lecithin, rapeseed lecithin or egg yolk lecithin. Using the raw material lecithin as the substrate, phosphatidyl-L-serine can be produced by utilizing transphosphatidylation.

18 Claims, No Drawings

CEREBRATION IMPROVER

This is a division of application Ser. No. 08/556,862 filed Nov. 2, 1995, now U.S. Pat. No. 5,900,409.

BACKGROUND OF THE INVENTION

1. Field of the Invention

The present invention relates to a composition having an effect of improving cerebration. More specifically, the present invention relates to a cerebration improver effective for the prophylaxis and treatment of Parkinson's disease and dementia such as Alzheimer's disease.

2. Description of the Related Art

A. Bruni, et al. report that the brain glucose level in mice injected via the caudal vein with phosphatidylserine extracted from bovine brain is increased by about 4 fold the level in the control group (A. Bruni et al., Nature, Vol. 260, p. 331, 1976).

A. Zanotti et al. also report that the oral administration of phosphatidylserine extracted from bovine brain to aged rats with memory deficits for 12 weeks improved the performance of the aged rats (A. Zanotti et al., Psychopharmacology Berl., Vol. 99, P. 316, 1989).

Furthermore, it is confirmed at a double-blind placebo-controlled clinical trial for humans the efficacy of phosphatidylserine extracted from bovine brain in improving the memory impairment in Alzheimer's disease and during the aging stage (P. J. Delwaide et al., Acta Neurol. Scand., Vol. 73, p. 136, 1986; R. R. Engel et al., Eur. Neuropsychopharmacol., Vol. 2, p. 149, 1992; T. Cenacci et al., Aging Clin. Exp. Res., Vol. 5, p. 123, 1993).

As has been described above, bovine brain-derived phosphatidylserine having the effect of increasing brain glucose level has an effect of improving the cerebration in rats and humans. Therefore, it is indicated that the degree of the increase in brain glucose level is an important indicator for selecting a substance with the action of improving cerebration. However, it is reported in the paper of A. Bruni et al. that the phosphatidylserine extracted from soy bean does not have such action. Hence, it is generally believed that the fatty acid composition of phosphatidylserine is a significant factor for exerting the action of improving cerebration.

More specifically, phosphatidylserine extracted from bovine brain has a highly characteristic fatty acid composition such that the structural fatty acid chain thereof contains higher levels of stearic acid chain at position α and oleic acid chain at position β. Generally, it has been believed currently that the specific structural fatty acid chain is essential for the expression of the action of improving cerebration.

Alternatively, Japanese Patent Laid-open No. 6-279311 describes that phosphatidylserine of a type with a synthesized specific fatty acid chain is promising for use in the treatment of senile dementia on the basis of its action activating protein kinase C-isozyme, but the efficacy has not yet been confirmed in vivo.

As to phosphatidylserine of the lyso type, lysophosphatidyl-L-serine derived from bovine brain-derived phosphatidylserine has an action for increasing the level of brain glucose and/or blood glucose (H. W. Chang et al., Br. J. Pharmacol., Vol. 93, p. 647, 1988).

Thus, it has been believed that phosphatidylserine extracted from bovine brain has an action of increasing brain glucose level owing to the specific fatty acid composition.

As has been mentioned above, conventionally known references have indicated that only phosphatidylserine extracted from bovine brain or lysophosphatidylserine has the action of increasing brain glucose level. However, it is with no doubt that phosphatidylserine extracted from bovine brain has severe limits from the respect of cost and supply scale because only about 1 g of phosphatidylserine can be available from the brain of a cow.

SUMMARY OF THE INVENTION

It is an object of the present invention to provide a cerebration improver having an action of improving cerebration with no occurrence of any problem from the respect of cost and supply.

According to the research work of the present inventors, it is confirmed that phosphatidylserine produced by using an enzymatic transphosphatidylation of at least one raw material lecithin selected from the group consisting of soybean lecithin, rapeseed lecithin, and egg yolk lecithin, as well as lysophosphatidyl-L-serine produced by the transphosphatidylation of the raw material lecithin or the hydrogenated product thereof with phospholipase $A_2$ in the presence of L-serine, has prominent effects of increasing brain glucose level and improving memory impairment.

A cerebration improver of one embodiment of the present invention contains phosphatidyl-L-serine or the salt thereof as the effective ingredient, wherein the phosphatidyl-L-serine has a structural fatty acid chain derived from at least one raw material lecithin selected from the group consisting of soy bean lecithin, rapeseed lecithin, and egg yolk lecithin.

A cerebration improver of another embodiment of the present invention contains phosphatidyl-L-serine or the salt thereof as the effective ingredient, wherein the phosphatidyl-L-serine has a structural fatty acid chain derived from at least one raw material lecithin selected from the group consisting of soybean lecithin, rapeseed lecithin, and egg yolk lecithin, and wherein the structural fatty acid chain is a hydrogenated saturated fatty acid chain.

A cerebration improver of a further embodiment of the present invention contains lysophosphatidyl-L-serine or the salt thereof as the effective ingredient, wherein the lysophosphatidyl-L-serine is composed of phosphatidyl-L-serine with the fatty acid chain thereof at position α or β being eliminated and the phosphatidyl-L-serine has a structural fatty acid chain derived from at least one raw material lecithin selected from the group consisting of soybean lecithin, rapeseed lecithin, and egg yolk lecithin.

A cerebration improver of a still further embodiment of the present invention contains lysophosphatidyl-L-serine or the salt thereof as the effective ingredient, wherein the lysophosphatidyl-L-serine is composed of phosphatidyl-L-serine with the fatty acid chain thereof at position α or β being eliminated and the phosphatidyl-L-serine has a structural fatty acid chain derived from at least one raw material lecithin selected from the group consisting of soybean lecithin, rapeseed lecithin, and egg yolk lecithin and the structural fatty acid chain is a hydrogenated saturated fatty acid chain.

In accordance with the present invention, the cerebration improver containing, as the effective ingredient, phosphatidyl-L-serine having a structural fatty acid chain derived from soybean lecithin, rapeseed lecithin or egg yolk lecithin or lysophosphatidyl-L-serine composed of phosphatidyl-L-serine with the fatty acid chain thereof at position α or β being eliminated, has a remarkable action for increasing the brain glucose level, whereby the improver has an effect of improving the cerebration of a subject administered with the improver. The cerebration improver in accordance with the present invention may contain as the effective ingredient the salt of the phosphatidyl-L-serine or the lysophosphatidyl-L-serine composed of the rearranged phosphatidyl L-serine with the fatty acid chain thereof at position α or β being eliminated, and such salt may be used satisfactorily if the salt is in the form of a pharmaceutically acceptable salt. Specific salts includes sodium salts, potassium salts, magnesium salts, ammonium salts, phosphate salts, hydrochloride salts, sulfate salts and the like, and preference is given to sodium salts and potassium salts among these salts.

The cerebration improver of the present invention may be administered effectively via intraveneous administration and oral administration. The improver may be mixed with other excipients such as additional phospholipids, sugar and protein to prepare capsules and granules with improved handling and shelf life. Because of the absence of any safety problem, the improver may be blended into daily foods and beverages, for use in improving and preventing cerebration disorders.

The aforementioned phosphatidyl-L-serine and lysophosphatidyl-L-serine as the effective ingredients in accordance with the present invention are both produced by the transphosphatidylation with phospholipase D using as the substrate soybean lecithin, rapeseed lecithin or egg yolk lecithin.

The process will now be illustrated. A raw material lecithin (namely, phosphatidylcholine) selected from soybean lecithin, rapeseed lecithin and egg yolk lecithin is subjected to the process of transphosphatidylation with phospholipase D in the presence of L-serine, thereby substituting the choline group with the serine group, to produce the rearranged phosphatidyl-L-serine.

If the structural fatty acid chain from the raw material lecithin selected from soybean lecithin, rapeseed lecithin and egg yolk lecithin is an unsaturated fatty acid, the unsaturated fatty acid is preferably converted into a saturated fatty acid via the hydrogenation process. The hydrogenation process may be applicable to the raw material lecithin prior to the transphosphatidylation; otherwise, the hydrogenation process may be applicable to the phosphatidyl-L-serine produced by the transphosphatidylation.

Lysophosphatidyl-L-serine may be produced by eliminating the fatty acid chain at either position α or β of the phosphatidyl-L-serine thus produced or of the hydrogenated phosphatidyl-L-serine. Using a raw material lysolecithin produced by eliminating the fatty acid molecule bound to the position α or β of the glycerol of the raw material lecithin selected from soybean lecithin, rapeseed lecithin and egg yolk lecithin, the process of transphosphatidylation described above is promoted to produce lysophosphatidyl-L-serine. Then, the cost for such elimination is low with no occurrence of any problem from the respect of scale-up supply.

Any commercially available soybean lecithin, rapeseed lecithin or egg yolk lecithin may be used, with no limitation, as the raw material. As phospholipase D for use in the process of transphosphatidylation, use may be made of for example those from cabbage and actinomyces, if they have an activity on lecithin or hydrogenated lecithin or lysolecithin in the presence of L-serine to produce phosphatidyl-L-serine.

Specific process of transphosphatidylation is known and described in for example Japanese Patent Laid-open No. 63-245685, so no detailed explanation is not described herein. The transphosphatidylation in the presence of an organic solvent such as ethyl acetate is recommended as the process of producing the cerebration improver of the present invention, because of a higher conversion yield and simple post-treatment.

Preferably, phosphatidyl-L-serine produced by the process of transphosphatidylation should be subjected to an appropriate purification process to remove impurities. As long as no disadvantage occurs such as the adverse effects from the administration and the inhibition of the cerebration improving action, the presence of impurities derived from the raw material or impurities contaminated during the process may not be problematic at all, if the content of such impurities is within the acceptable range.

DESCRIPTION OF THE PREFERRED EMBODIMENTS

EXAMPLE 1—1

Using soybean lecithin as the raw material, phosphatidyl-L-serine was produced by the following process.

Soybean lecithin (50 g; PC 80, BOLEC as the product name; Croklaan B.V., Netherlands) and soybean oil (10 g) were placed in a 300-ml vial, followed by addition of ethyl acetate (50 ml) for solubilization. Adding a solution (20 ml) of 0.30 g/ml L-serine dissolved in 0.1 M sodium phosphate buffer, pH 7.0 to the resulting solution for thorough blending, a solution of 500 U/ml phospholipase D from actinomyces (15 ml; manufactured by Yakult Honsha, Co., Ltd.) was added to the mixture solution for reaction at 50° C. for 5 hours under stirring with a stirrer.

So as to inactive the enzyme in the reaction solution, the vial containing the reaction solution was immersed in hot water. Subsequently, the reaction solution was cooled in ice to separate the solution into two layers, which were then left to stand for 30 minutes. Subsequently, the upper layer was discarded. The remaining lower layer was extracted in chloroform, which was then dried under reduced pressure. Chloroform (15 ml) was added to the resulting product (5 g) for dissolution. The resulting solution was then applied to a column (of a 32-mm diameter×a 300-mm length) packed with silica gel (Silica Gel 60 as the product name; manufactured by Merck Japan Ltd.) to separate a fraction containing phosphatidyl-L-serineusingchloroform-methanol (4:1) at a flow rate of 100 ml/hr at room temperature.

EXMAPLE 1-2

Using egg yolk lecithin (PL-100LE as the product name; manufactured by Q. P. Corp. Japan) as the substrate, rearranged phosphatidyl-L-serine was produced by the same method as in Example 1—1.

EXAMPLE 1-3

Using rapeseed lecithin as the raw material, phosphatidyl-L-serine was produced by the following method.

85% Ethanol (4.8 kg) was added to rapeseed lecithin (1.2 kg; manufactured by Rinoru Oil Mills Co., Ltd. Japan) and sufficiently homogenized with a homogenizer. Subsequently, the resulting homogenate was left to stand at room temperature for 2 hours to separate the supernatant, which was then dried under reduced pressure to recover an ethanol-soluble fraction (about 300 g). To a part (120 g) of the fraction was added ethyl acetate (600 g) for stirring and blending, which was then left to stand overnight at 5° C. The ethyl acetate-insoluble fraction precipitated through the procedure was then dried under reduced pressure, to recover rapeseed lecithin of a higher phosphatidylcholine content (the fraction of rapeseed lecithin of about 70 g).

Using the fraction of rapeseed lecithin as the substrate, rearranged phosphatidyl-L-serine was produced by the same method as in Example 1—1.

EXAMPLE 2-1

Soybean lecithin (LECINOL S-10EX as the product name; Nikko Chemicals Co., Ltd.) was processed for hydrogenation. Using the hydrogenated soybean lecithin as the substrate, phosphatidyl-L-serine was produced by the same method as in Example 1—1.

EXAMPLE 2—2

The soybean lecithin-derived phosphatidyl-L-serine (1 g) produced in Example 1—1, was solubilized in a mixture solution of n-hexane (15 g) and ethanol (3 g). Adding 10% palladium carbon (0.15 g) to the solution, the resulting solution was processed for hydrogenation for about 5 hours under stirring under the conditions of room temperature and ambient pressure.

EXAMPLE 3-1

From the individual types of phosphatidyl-L-serine produced in Examples 1—1 to 2—2, lysophosphatidyl-L-serine was produced as described hereinbelow.

More specifically, each type of phosphatidyl-L-serine (300 mg) was charged in a 6-ml vial, followed by addition of ethyl acetate (1.2 ml), 0.25 M sodium phosphate buffer, pH 7.4 (0.20 ml), distilled water (1.2 ml) and 11,200 U/ml phospholipase $A_2$ from porcine pancreas (0.02 ml; "LECITASE 10L" as the product name; manufactured by Novo-Nordex Co., Ltd.) for sufficient blending, prior to reaction at 50° C. for 16 hours. The vial containing the reaction solution was then immersed in hot water for 20 minutes to inactivate the enzyme in the reaction solution. Subsequently, the solution was washed in acetone (3.0 ml×3). Then, the precipitate was recovered and dried in air to yield lysophosphatidyl-L-serine.

EXAMPLE 4

The compositions of the fatty acid chains of the individual types of phosphatidyl-L-serine and lysophosphatidyl-L-serine obtained in Example 1—1 to 3-1 were analyzed. According to the routine method, the analysis of a methyl esterified sample was carried out by gas-liquid chromatography (GLC) with a capillary column. The results are shown in Table 1 below. In Table 1, herein, "PS" means phophatidyl-L-serine; "LPS", lysophosphatidyl-L-serine; "16:0", palmitic acid; "18:0" means stearic acid; "18:1", oleic acid; "18:2", linoleic acid; and "18:3", linolenic acid.

TABLE 1

|  | 16:0 | 18:0 | 18:1 | 18:2 | 18:3 | Others |
| --- | --- | --- | --- | --- | --- | --- |
| BB-PS | 0.9 | 38.7 | 31.8 | — | — | 16.5 |
| BB-LPS (α) | 1.8 | 81.4 | 8.5 | — | — | 8.3 |
| RSB-PS | 13.8 | 3.9 | 10.2 | 63.2 | 5.9 | 3.0 |

TABLE 1-continued

|  | 16:0 | 18:0 | 18:1 | 18:2 | 18:3 | Others |
| --- | --- | --- | --- | --- | --- | --- |
| RSB-LPS (α) | 35.9 | 8.8 | 7.5 | 40.0 | 3.1 | 4.7 |
| HRSB-PS | 13.5 | 85.1 | 0.5 | — | — | 0.9 |
| REY-PS | 31.8 | 12.3 | 24.1 | 17.0 | 0.1 | 14.7 |

BB-PS: Bovine brain PS
BB-LPS: Bovine brain LPS
RSB-PS: Rearranged soybean PS
RSB-LPS: Rearranged soybean LPS
HRSB-PS: Hydrogenated rearranged soy bean PS
REY-PS: Rearranged egg yolk PS
(α): position α

As shown in Table 1, the fatty acids in the phosphatidyl-L-serine extracted from bovine brain were principally composed of stearic acid and oleic acid. On the contrary, the fatty acids in the rearranged phosphatidyl-L-serine from the raw material egg yolk lecithin were mostly composed of palmitic acid and oleic acid, while the fatty acids in the rearranged phosphatidyl-L-serine from the raw material soy bean lecithin were mainly composed of palmitic acid and linoleic acid. Thus, it is indicated that these types of rearranged phosphatidyl-L-serine have markedly different fatty acid compositions from those of the phosphatidyl-L-serine from bovine brain.

EXAMPLE 5

As will be described below, the effect of increasing brain glucose level via oral administration was confirmed at a test.
1. Preparation of a Sample for Administration To the phosphatidyl-L-serine (20 mg) produced via the process of transphosphatidylation from a substrate soy bean lecithin was added 250 mM phosphate buffer, pH 7.9 (1 ml), which was then emulsified with a homogenizer of a Potter type, followed by ultrasonication (at 0° C. for 8 minutes) to prepare a testing sample. A control sample was produced by adding 250 mM phosphate buffer, pH 7.9 (1 ml) to soybean lecithin (20 mg) followed by the process of emulsification and ultrasonication.
2. Sample Administration Within 2 hours after the preparation, the samples in emulsion were orally given to plural groups of male ICE mice (of body weight of about 35 g) at 1.0 ml/40 g (PS: 500 mg/kg) per mouse using a stomach probe.
3. Rapid Brain Freezing When a given period of time (30 minutes to 4 hours) passed after the administration, each group of the mice was decapitated and sacrificed to death. Their heads were charged in liquid nitrogen for rapid freezing.
4. Collection of Frozen Brain Each frozen murine head was halved in the median line with an autopsy chisel. Then, removing the tissues with the autopsy chisel excluding the anterior and posterior parts of brain and the upper and lower parts of brain, the brain was excised.
5. Extraction from Frozen Brain The total weight of the frozen brain of each mouse was weighed (300 to 400 mg), and pulverized in a mortar filled with liquid nitrogen. To the powder (100 mg) in the mortar was added 0.3 N perchloric acid (0.5 ml) for grinding into liquid with a pestle. The residue was centrifuged and discarded, to collect the supernatant. The supernatant was neutralized with 1 N potassium hydroxide, and the resulting precipitate potassium perchlorate was centrifuged and discarded to collect the supernatant of the extracted solution for storage under freezing.

6. Assay of Brain Glucose

Using an assay kit by the hexokinase method, the glucose level in the extracted solution stored under freezing was assayed. The results are shown in Table 2 below. In Table 2, herein, "PS" means phosphatidyl-L-serine.

TABLE 2 a vs b: p < 0.05 (Tschuky's multiple comparison)

| Experimental groups | Brain glucose level ($10^{-6}$ mol/g) |
|---|---|
| No administration | $0.7 \pm 0.2$ [a] |
| RSB-PS (30 min. after administration) | $2.7 \pm 1.8$ [b] |
| RSB-PS (1 hr. after administration) | $1.4 \pm 0.4$ [ab] |
| RSB-PS (2 hrs. after administration) | $1.3 \pm 0.4$ [ab] |
| RSB-PS (4 hrs. after administration) | $0.9 \pm 0.2$ [a] |
| SBL (2 hrs. after administration) | $0.7 \pm 0.2$ [a] |

SBL: Soy bean lecithin

As shown in Table 2, the rearranged soybean-derived phosphatidyl-L-serine, orally administered, increased the brain glucose level by about 4 fold 30 minutes after the administration that of the level in the case of no administration ($P<0.05$, Tschuky's multiple comparison). Subsequently, the glucose level was lowered as the time passed. Four hours after the administration, the level reached (was down to) the level in the case of no administration.

EXAMPLE 6

As will be described below, the effect of increasing brain glucose level via caudal vein injection was confirmed at a test.

1. Preparation of Various Types of Lysophosphatidyl-L-Serine

From the types of phosphatidyl-L-serine produced in Examples 1—1 to 2—2, various types of lysophosphatidyl-L-serine were produced in the following manner.

More specifically, each of the types of phosphatidyl-L-serine (300 mg) was placed in a 6-ml vial, followed by addition of ethyl acetate (1.20 ml), 0.1 M Tris-HCl buffer, pH 7.4 (1.20 ml), and 11,200 U/ml phospholipase $A_2$ (0.02 ml; "LECITASE 10L" as the product name; manufactured by Novo-Nordex Co. Ltd.) for sufficient blending, prior to reaction at 50° C. for 14 hours. Subsequently, released fatty acids were washed off in acetone, to recover lysophosphatidyl-L-serine.

2. Preparation of a Sample for Administration

To the various types of lysophosphatidyl-L-serine (2.0 mg or 6.0 mg) was added 250 mM phosphate buffer, pH 7.9 (1 ml), followed by emulsification with a homogenizer of Potter type and subsequent ultrasonication (at 0° C. for 8 minutes); to prepare samples.

3. Sample Administration

Within 2 hours after the preparation, the individual samples in emulsion were injected via the caudal vein into plural groups of male ICR mice (of body weight of about 35 g) at 1.0 ml/40 g (PS: 30 mg/kg) per mouse.

4. Rapid Brain Freezing

When a given period of time (30 minutes) passed after the administration, each group of the mice was decapitated and sacrificed to death. Their heads were charged in liquid nitrogen for rapid freezing.

5. Collection of Frozen Brain

For the extraction from the frozen heads and the assay of brain glucose, the same procedures were carried out as in Example 5. The results are shown in Table 3 below. In Table 3, herein, "LPS" means lysophosphatidyl-L-serine.

TABLE 3

A vs B vs C: p < 0.01 (Tschuky's multiple comparison)

| Experimental groups | Brain glucose level ($10^{-6}$ mol/g) |
|---|---|
| No administration | $0.8 \pm 0.2$ [A] |
| RSB-LPS (10 mg/kg) | $1.8 \pm 0.8$ [BC] |
| RSB-LPS (30 mg/kg) | $2.5 \pm 0.2$ [B] |
| HRSB-LPS | $3.0 \pm 0.4$ [BC] |
| REY-LPS | $2.7 \pm 0.5$ [BC] |
| BB-LPS (10 mg/kg) | $3.2 \pm 0.9$ [C] |

HRSB-LPS: Hydrogenated rearranged soybean LPS
REY-LPS: Rearranged egg yolk LPS
BB-LPS: Bovine brain LPS As shown in Table 3, lysophosphatidyl-L-serine of the types from soybean and egg yolk increased murine brain glucose significantly as in the case of lysophosphatidyl-L-serine from bovine brain.

EXAMPLE 7

In the following manner, the effect of improving memory impairment induced by scopolamine (SC) was confirmed.

To each group of 10 male SD rats weighing about 300 g was intraperitoneally administered a scopolamine solution (3.0 mg/ml of buffer) or a solution of each of the various types of phosphatidyl-L-serine (60 mg/ml of buffer), each at a dose of 1.0 ml/kg. Twenty minutes after the administration, the rats were placed in the light room of a step-through gage (manufactured by Muromachi Machinery Co., Ltd.). About 10 seconds later, opening the door separating the light room from the dark room, and immediately after the rats stepped into the dark room, 2-second electric shock (4 mA, 100 V, DC) was given to the rats. Then, 24 hours after the administration, the rats were again placed in the light room, to count the reaction latent time up to the maximum 5 minutes until the four limbs were all placed in the dark room. It is determined that a longer reaction latent time indicates better memory of the experience of electric shock. The results are shown in Table 4. In Table 4, herein, "PS" means phosphatidyl-L-serine; "LPS", lysophosphatidyl-L-serine; and "SC" means scopolamine.

TABLE 4 a vs b: p < 0.01 (Mann-Whitney's U-Test)
A vs B: p < 0.01 (Non-parametric multiple comparison)

| Experimental groups | SIR [*1] | RLT [*2] (sec.) |
|---|---|---|
| Control [*3] | 0/10 [aA] | 300 or more |
| SC alone | 9/10 [bB] | 128 |
| SC + BB-PS | 0/10 [A] | 300 or more |
| SC + RSB-PS | 0/10 [A] | 300 or more |
| SC + HRSB-PS | 0/10 [A] | 300 or more |
| SC + RR-PS | 0/10 [A] | 300 or more |
| SC + REY-PS | 0/10 [A] | 300 or more |
| SC + BB-LPS | 0/10 [A] | 300 or more |
| SC + RSB-LPS | 0/10 [A] | 300 or more |

[*1] Stepping-in ratio; a retio of the number of rats stepping into dark room within 5 minutes to the total number of rats.
[*2] Reaction latent time in dark room (median).
[*3] Administrated with buffer solution.
RR-PS: Rearranged rapeseed PS As shown in Table 4, phosphatidyl-L-serine of the types derived from soy bean, rapeseed and egg yolk has the effect of improving memory impairment induced by scopolamine at approximately the same extent as in the case of phosphatidyl-L-serine from bovine brain.

As has been described above, the cerebration improver containing phosphatidyl-L-serine from soybean, rapeseed or egg yolk as the effective ingredient in accordance with the present invention can be continuously administered readily with no pain because phosphatidyl-L-serine effective for improving cerebration can be orally ingested from the improver. Furthermore, the phosphatidyl-L-serine effective for improving cerebration can be produced at less cost and additionally at a large scale, by utilizing transphosphatidylation via a phospholipid degradation enzyme (phospholipase D).

What is claimed is:

1. A cerebration improver comprising lysophosphatidyl-L-serine or a salt thereof as the effective ingredient, wherein the lysophosphatidyl-L-serine contains phosphatidyl-L-serine with the fatty acid chain thereof at position α or β being eliminated and the phosphatidyl-L-serine has a structural fatty acid chain derived from at least one raw material lecithin selected from the group consisting of soybean lecithin, rapeseed lecithin and egg yolk lecithin, and which is produced by a transphosphatidylation with phospholipase D in the presence of L-serine.

2. The cerebration improver of claim 1 which also contains a pharmaceutical or food excipient.

3. A method for improving cerebration in a patient in need thereof comprising administering to said patient an effective amount of the cerebration improver of claim 1.

4. A method for improving cerebration in a patient in need thereof by increasing the brain glucose level of said patient, comprising administering an effective amount of the cerebration improver of claim 1 to said patient.

5. The cerebration improver of claim 1, wherein the raw material lecithin is soybean lecithin.

6. The cerebration improver of claim 1, wherein the raw material lecithin is rapeseed lecithin.

7. The cerebration improver of claim 1, wherein the raw material lecithin is egg yolk lecithin.

8. The cerebration improver of claim 1, wherein the effective ingredient is a salt of lysophosphatidyl-L-serine, and said salt is selected from the group consisting of a sodium salt, a potassium salt, a magnesium salt, a hydrochloride salt and a sulfate salt.

9. The cerebration improver of claim 8, wherein the salt is selected from the group consisting of a sodium salt and a potassium salt.

10. A cerebration improver comprising lysophosphatidyl-L-serine or a salt thereof as the effective ingredient, wherein the lysophosphatidyl-L-serine contains phosphatidyl-L-serine with the fatty acid chain thereof at position α or β being eliminated and the phosphatidyl-L-serine has a structural fatty acid chain derived from at least one raw material lecithin selected from the group consisting of soybean lecithin, rapeseed lecithin and egg yolk lecithin, and which is produced by a transphosphatidylation and phospholipase D in the presence of L-serine, and wherein the structural fatty acid chain is a hydrogenated saturated fatty acid chain.

11. The cerebration improver of claim 10 which also contains a pharmaceutical or food excipient.

12. A method for improving cerebration in a patient in need thereof comprising administering to said patient an effective amount of the cerebration improver of claim 10.

13. A method for improving cerebration in a patient in need thereof by increasing the brain glucose level of said patient, comprising administering an effective amount of the cerebration improver of claim 10 to said patient.

14. The cerebration improver of claim 10, wherein the raw material lecithin is soybean lecithin.

15. The cerebration improver of claim 10, wherein the raw material lecithin is rapeseed lecithin.

16. The cerebration improver of claim 10, wherein the raw material lecithin is egg yolk lecithin.

17. The cerebration improver of claim 10, wherein the effective ingredient is a salt of lysophosphatidyl-L-serine, and said salt is selected from the group consisting of a sodium salt, a potassium salt, a magnesium salt, a hydrochloride salt and a sulfate salt.

18. The cerebration improver of claim 17, wherein the salt is selected from the group consisting of a sodium salt and a potassium salt.

* * * * *